(12) United States Patent
Haskins et al.

(10) Patent No.: US 11,701,125 B2
(45) Date of Patent: Jul. 18, 2023

(54) SURF LEASH TOURNIQUET DEVICE AND RELATED METHODS

(71) Applicants: Claude Haskins, San Diego, CA (US); Sean Doherty, San Diego, CA (US); Wayne Husband, San Diego, CA (US)

(72) Inventors: Claude Haskins, San Diego, CA (US); Sean Doherty, San Diego, CA (US); Wayne Husband, San Diego, CA (US)

(*) Notice: Subject to any disclaimer, the term of this patent is extended or adjusted under 35 U.S.C. 154(b) by 28 days.

(21) Appl. No.: 17/507,667

(22) Filed: Oct. 21, 2021

(65) Prior Publication Data

US 2022/0151636 A1 May 19, 2022

Related U.S. Application Data

(63) Continuation of application No. 15/882,950, filed on Jan. 29, 2018, now abandoned.

(60) Provisional application No. 62/451,571, filed on Jan. 27, 2017.

(51) Int. Cl.
*A61B 17/132* (2006.01)
*B63B 32/73* (2020.01)
*B63B 32/77* (2020.01)

(52) U.S. Cl.
CPC ...... *A61B 17/1322* (2013.01); *A61B 17/1327* (2013.01); *B63B 32/73* (2020.02); *B63B 32/77* (2020.02)

(58) Field of Classification Search
CPC . A61B 17/1322; A61B 17/1327; B63B 32/73; B63B 32/77
See application file for complete search history.

(56) References Cited

U.S. PATENT DOCUMENTS

| | | | | |
|---|---|---|---|---|
| 4,234,990 A | * | 11/1980 | Colburn | B63B 32/70 441/75 |
| 5,194,026 A | * | 3/1993 | Corwin | B63B 32/70 441/75 |
| 2010/0057120 A1 | * | 3/2010 | Kirkham | A61B 17/1322 606/203 |
| 2010/0160957 A1 | * | 6/2010 | Kirkham | F16G 11/14 24/115 J |
| 2010/0286724 A1 | * | 11/2010 | Rose | A61B 17/1322 606/203 |

* cited by examiner

*Primary Examiner* — Jung Rui Ou
(74) *Attorney, Agent, or Firm* — Buche & Associates, P.C.; John K. Buche; Bryce A. Johnson

(57) ABSTRACT

Generally disclosed is a surf leash with a tourniquet device that allows the cord of the surf leash to be convertible into a tourniquet and related methods of use.

2 Claims, 12 Drawing Sheets

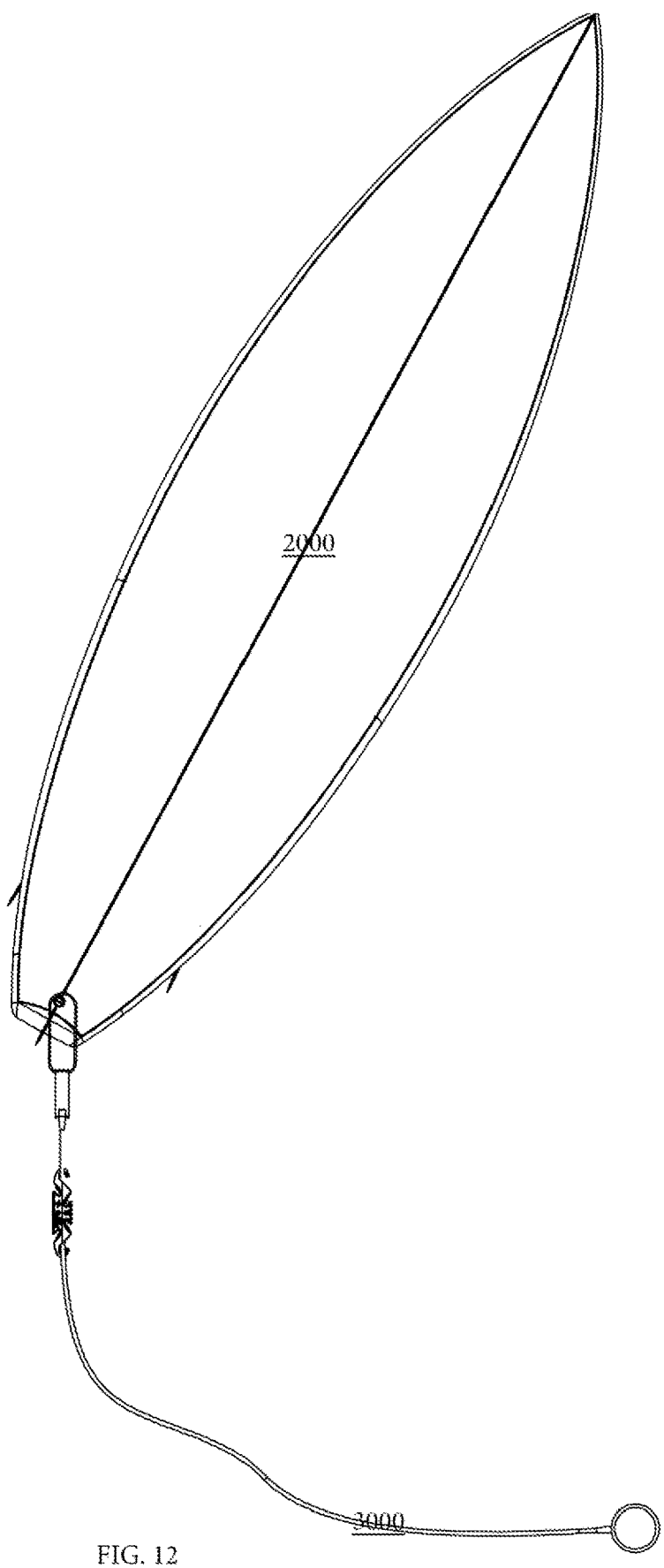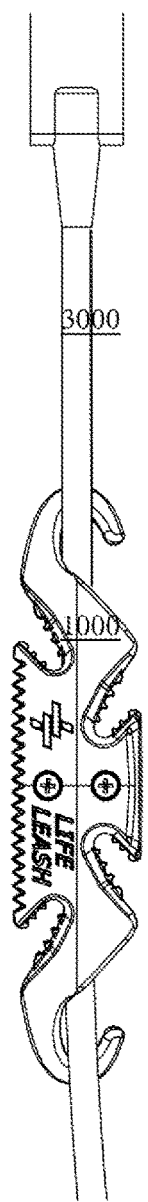
FIG. 12
FIG. 13A

SURF LEASH TOURNIQUET DEVICE AND RELATED METHODS

CROSS-REFERENCE TO RELATED APPLICATIONS

This application is a continuation of U.S. patent application Ser. No. 15/882,950, now abandoned, which claims the priority and benefit of U.S. Prov. App. Ser. No. 62/451,571 (filed Jan. 27, 2017) for a "surf leash tourniquet device and related methods." This provisional document is hereby incorporated by reference in its entirety.

STATEMENT REGARDING FEDERALLY SPONSORED RESEARCH OR DEVELOPMENT

Not applicable.

BACKGROUND OF THE INVENTION

Field of Invention

The present disclosure pertains to the field of surf leashes.

Background of the Invention

Surf leashes are used by surfers to attach the surfer's foot to the surfboard so that the board does not stray away from the surfer in the water. Common surf leashes are comprised of a urethane cord with a quick release device on each end of the cord, with one end attached to the surfer's ankle and the other end attached to the surfboard.

Surfers are exposed to a lot of dangers in the water and a surfer's limbs and extremities can be vulnerable to being injured without any first aid help nearby. Some of the risks that surfers are exposed to are rocks, reefs, and well documented shark attacks. Most shark attacks on surfers occur when the shark mistakes a surfer for prey. When a shark realizes the surfer is not its usual meal, it will sometimes release the surfer from its bite, however the blood loss from the resulting injury may prove fatal.

One common first aid device for wounded extremities is a tourniquet, which is a constricting or compressing device that is used to control blood circulation to an extremity for a period of time. A tourniquet is extremely important to control bleeding in cases of extreme blood loss. When a surfer injures an extremity, having a tourniquet within reach could be life-saving; however, in many instances, finding an operational or improvisational tourniquet is difficult and can waste valuable time in saving a surfer's life or limb. Thus, there exists a need for a surf leash that can operate as a fully functional tourniquet, so that a tourniquet is always within reach. Specifically, there is a need for a surf leash with a tourniquet device for surfers in remote areas without ready access to lifeguards and paramedics.

There are some embodiments of devices which are able to operate as tourniquets. For example, Girton (U.S. Pat. No. 2,812,123) discloses a gun sling that is removable from a gun and convertible into a tourniquet. Additionally, Brub (US 20120215254) discloses a belt that is operable as a tourniquet. However, there is yet to be a functional tourniquet that is readily available to surfers out in the water. Therefore, there exists a need for a surf leash that is convertible to a tourniquet.

SUMMARY OF THE INVENTION

An objective of the present invention is to provide a surf leash that also operates as a tourniquet.

BRIEF DESCRIPTION OF THE FIGURES

Other objectives of the disclosure will become apparent to those skilled in the art once the invention has been shown and described. The manner in which these objectives and other desirable characteristics can be obtained is explained in the following description and attached figures.

FIG. 12 is an environmental view of the leash tourniquet device;
FIG. 13A is an environmental view of the leash tourniquet device.

DETAILED DESCRIPTION OF PREFERRED EMBODIMENTS

Generally disclosed is a surf leash tourniquet that features a rigid tourniquet device to allow the surf leash's cord to function as a tourniquet. In one mode of use as a tourniquet, the leash of a surfboard may be provided through a central bore of the surf leash, wrapped around an appendage of a surfer, provided through a hook or other cord receiver, constricted around the appendage via twist action on the tourniquet device around the central bore of the tourniquet device. The more specific details of the tourniquet device are disclosed with reference to the figures.

Figure 1:
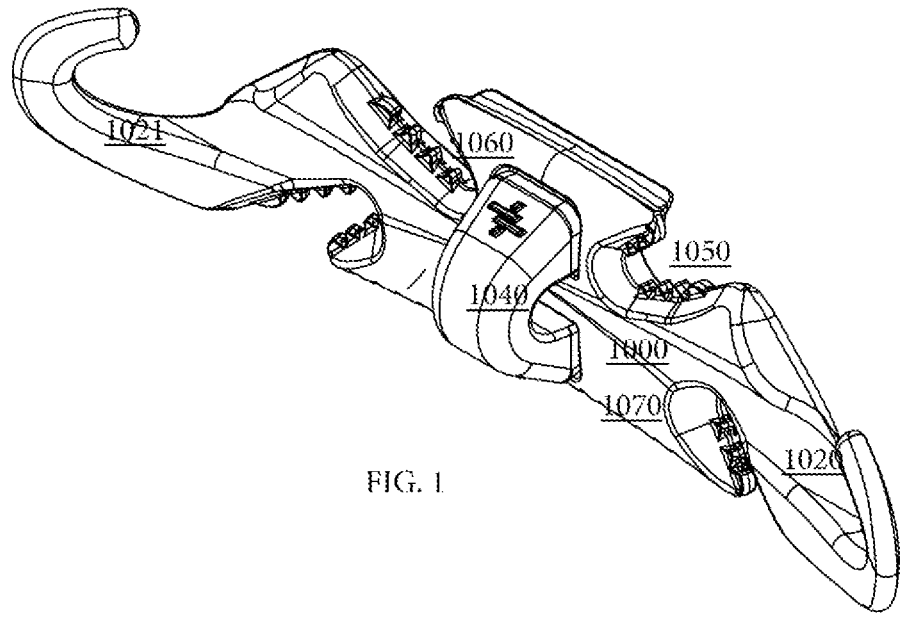
FIG. 1. is a top perspective of a leash tourniquet device.
Figure 2:
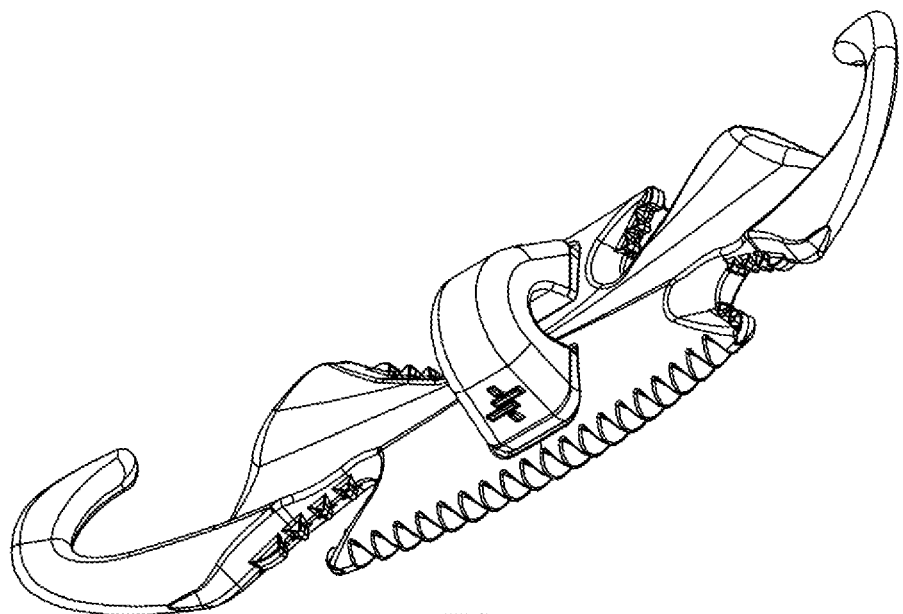
FIG. 2 is a bottom perspective view of the leash tourniquet device.
Figure 3:
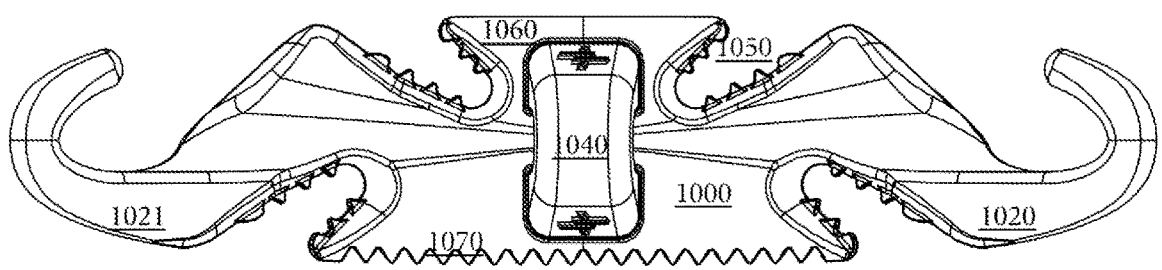
FIG. 3 is a front view of the leash tourniquet device.
Figure 4:
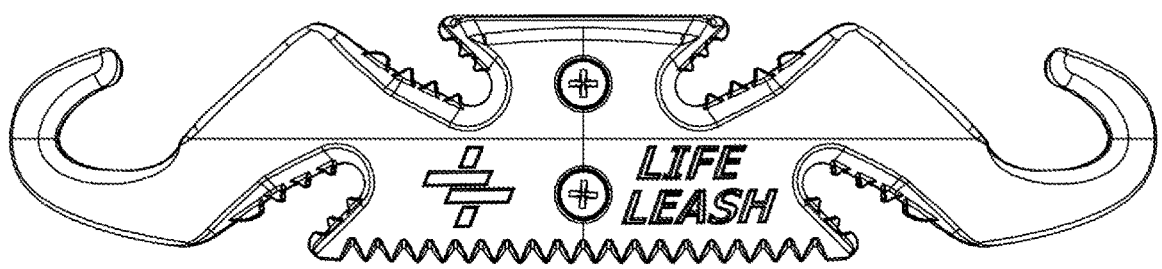
FIG. 4 is a back view of the leash tourniquet device.
Figure 5:
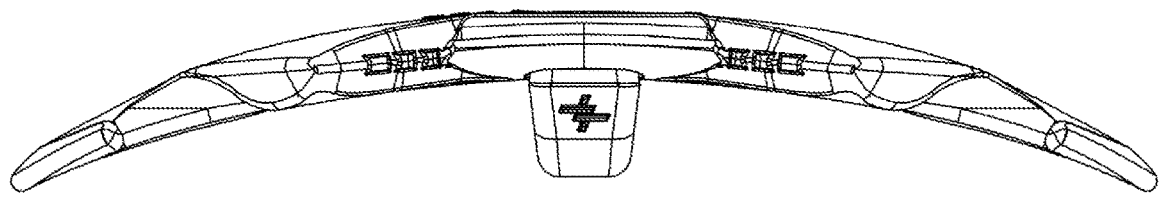
FIG. 5 is a top view of the leash tourniquet device.
Figure 6:
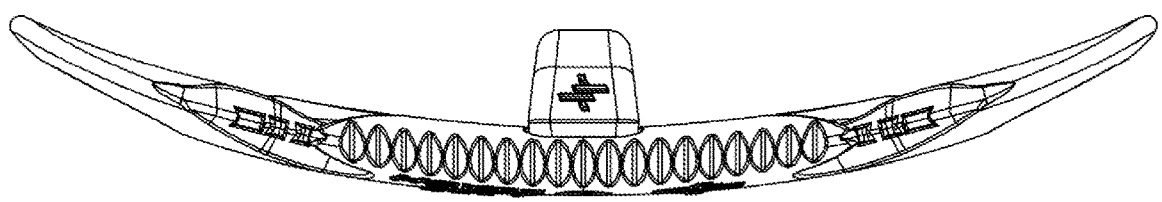
FIG. 6 is a bottom view of the leash tourniquet device.
Figure 7:
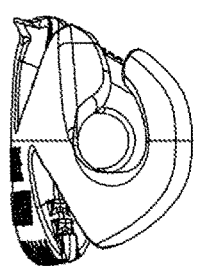
FIG. 7 is a right-side view of the leash tourniquet device.
Figure 8:
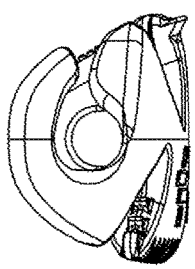
FIG. 8 is a left-side view of the leash tourniquet device.
Figures 9, 10:
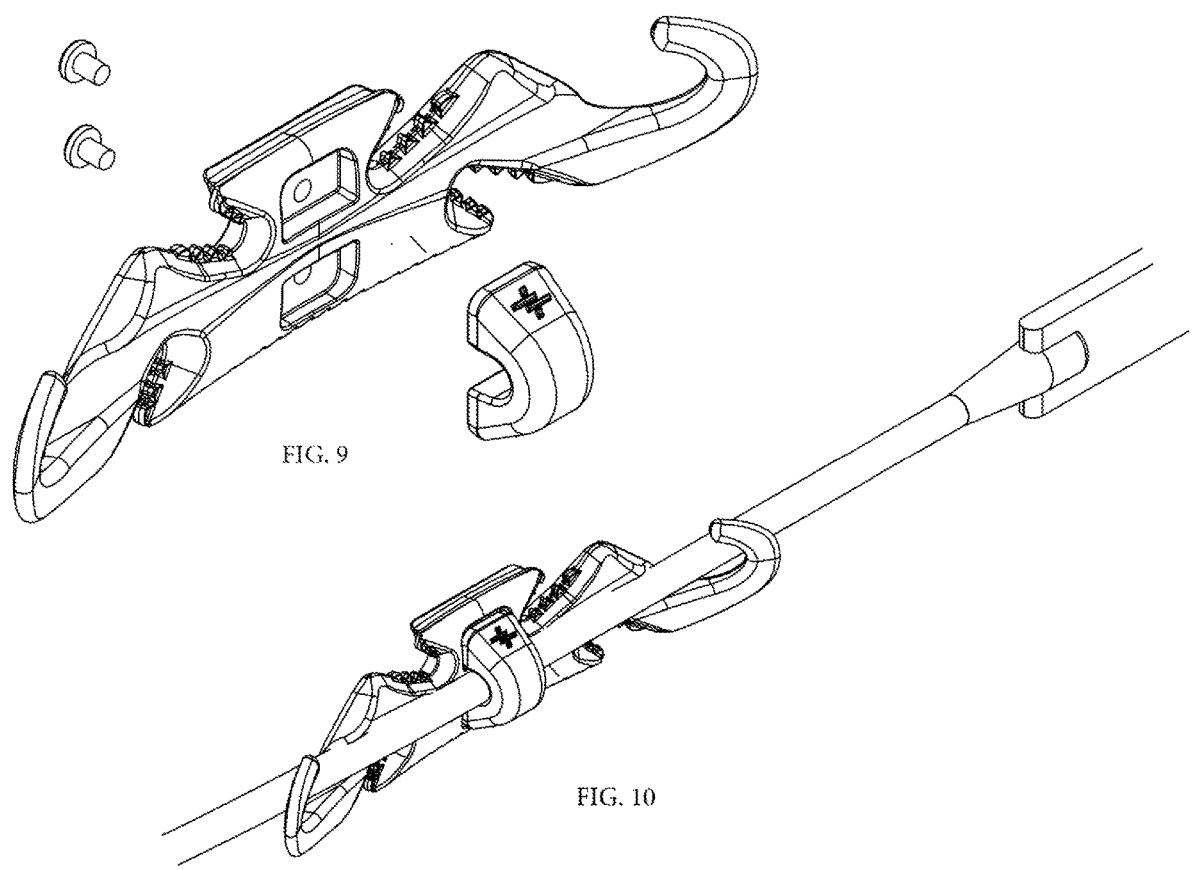
FIG. 9 is an exploded perspective view of the leash tourniquet device.
FIG. 10 is an environmental view of the leash tourniquet device.

FIG. 1 is a top perspective of the leash tourniquet 1000. FIG. 2 is a bottom perspective view of the leash tourniquet 1000. FIG. 3 is a front view of the leash tourniquet 1000. FIG. 4 is a back view of the leash tourniquet 1000. FIG. 5 is a top view of the leash tourniquet 1000. FIG. 6 is a bottom view of the leash tourniquet 1000. FIG. 7 is a right-side view of the leash tourniquet 1000. FIG. 8 is a left-side view of the leash tourniquet 1000. FIG. 9 is an exploded view of the tourniquet device 1000.

As shown in FIGS. 1-9, the tourniquet device 1000 may be composed of: a first receiver 1020, a second receiver 1021, wherein the first and second receiver 1020, 1021 may be hooks; a central bore 1040; four anchor slots 1050; a scraper 1060; and a wax trowel 1070. Suitably, the tourniquet device 1000 may be formed of a concave elliptical disk with hooks or receivers 1020, 1021 defined along the semi-major access, the bore 1040 centrally positioned, the anchor slots 1050 defined by oblique cut outs relative to the semi-minor and semi-major axes of the general elliptical tourniquet device, and the scraper 1060 and trowel 1070 defined by the edge of the device 1000 on the co-vortexes of the elliptical body. As shown in FIG. 9, the bore 1040 may be fastened via screws through the center of the body. As shown in FIGS. 7 and 8, the hooks 1020,1021 are cutout so that the concavity results in the hooks and bore 1040 are positioned in substantial alignment, whereby a leash or cord can pass through both hooks 1020, 1021 and the bore 1040 in an unobstructed manner. The hook and slots may have teeth to grip a cord.

Figure 11:
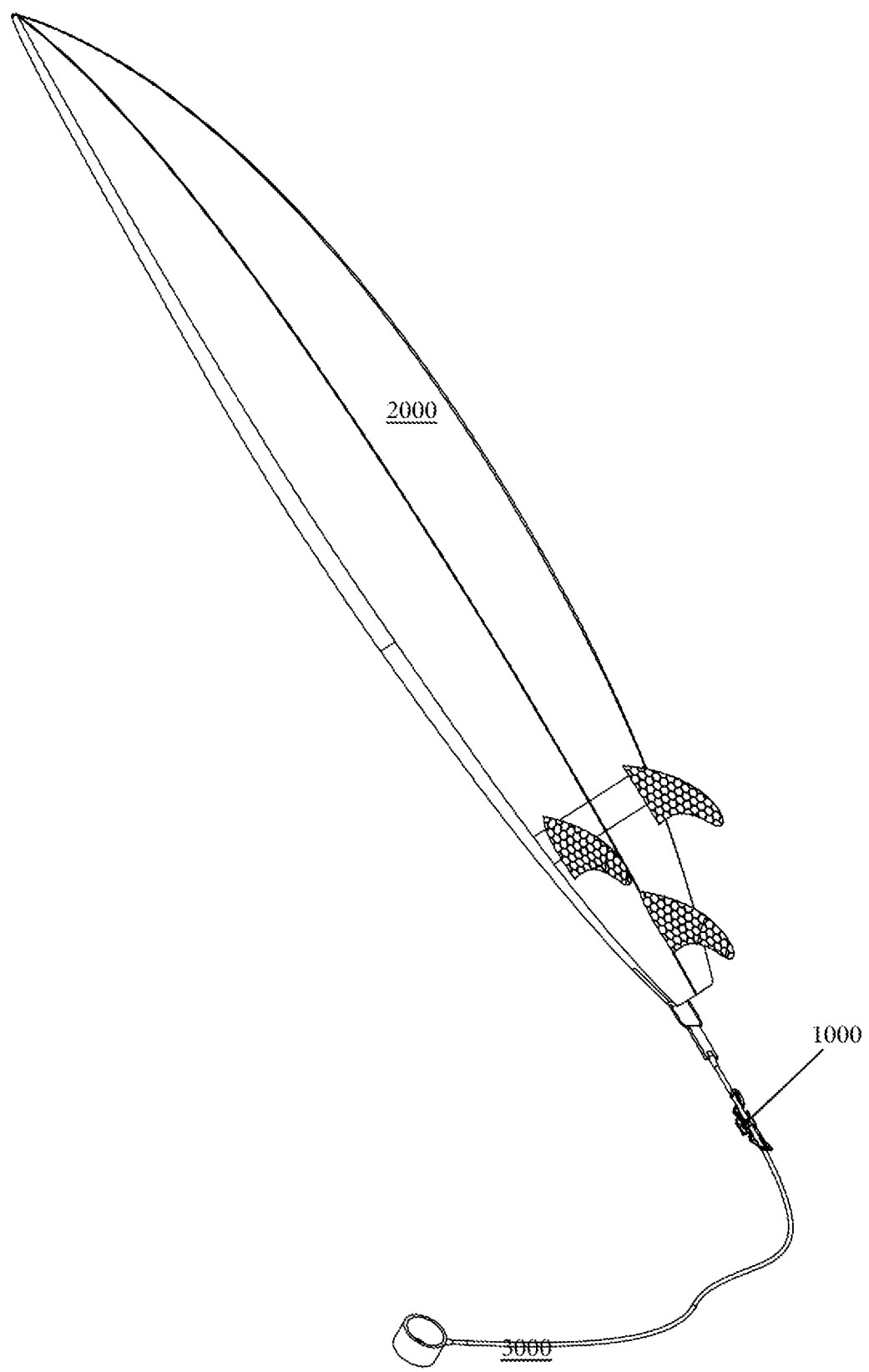
FIG. 11 is an environmental view of the leash tourniquet device.

FIG. 10 is a perspective view of one embodiment of the surf leash tourniquet 1000 of FIGS. 1-9. FIGS. 11 and 12 are contextual views of the surf leash tourniquet device 1000 installed on a leash 3000 of a surfboard 2000. FIG. 13A is another perspective view of the device 1000 on a surf leash 3000 of a surf board 2000. Referring to FIG. 10-13, a tourniquet device 10 may be disposed along a surf leash by threading the cord 3000 through the bore 1040 of a tourniquet device 1000 and threading the cord 3000 along the hooks 1020, 1021 i.e. the first and second receiver 1020, 1021.

Figure 13B:
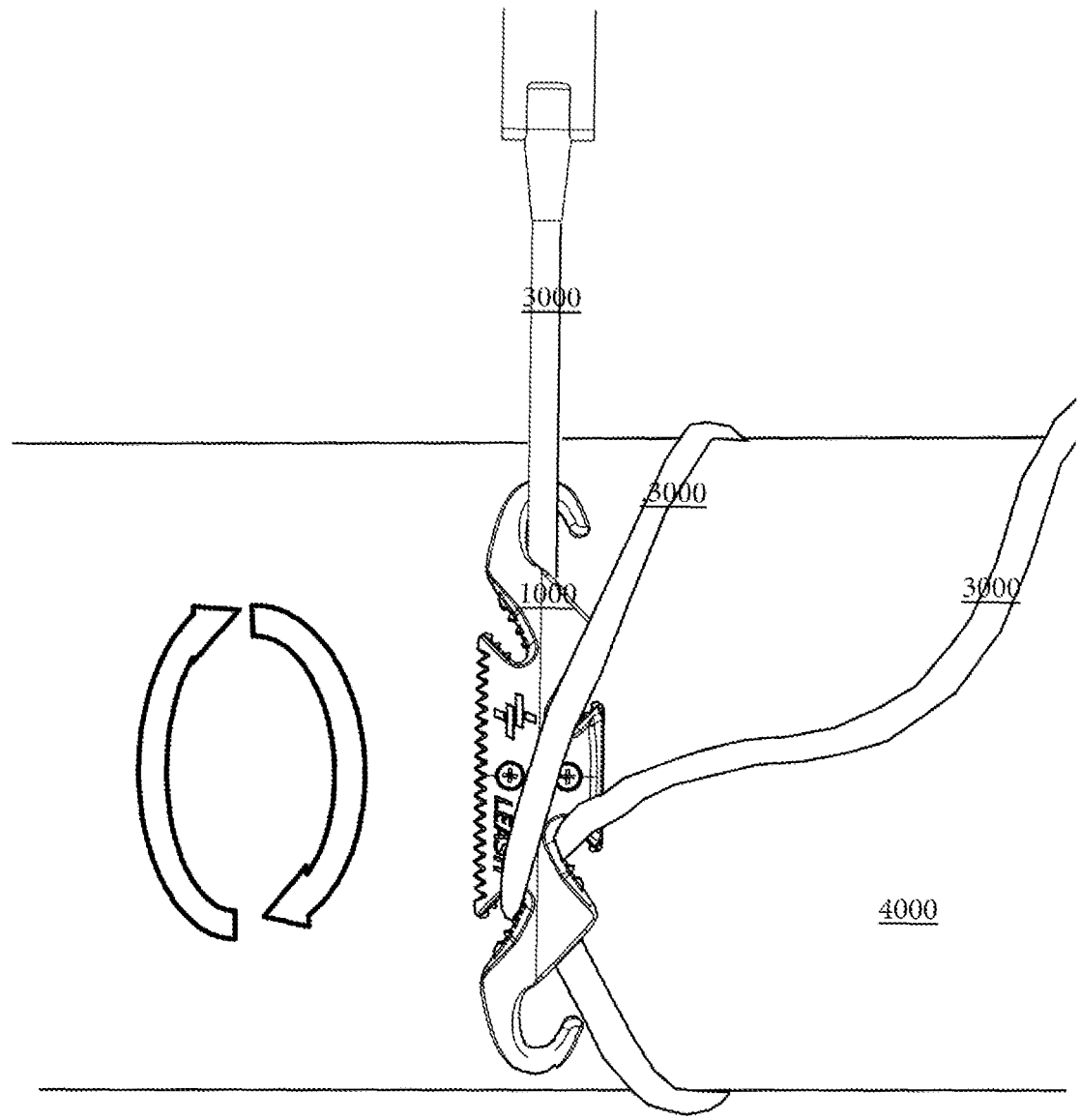
FIG. 13B is an environmental view of the leash tourniquet device on an appendage of a surfer.

FIG. 13B is an environmental view of the surf leash tourniquet on an appendage 4000 of a user. As shown, a user may use the surf leash 3000 as a tourniquet by wrapping the cord 3000 around the extremity or appendage 4000 to a desired tightness and then wrapping the excess cord 3000 around at least one of the hooks of the first and second receiver 1020, 1021 before anchoring the cord 3000 in an anchor slot and turning the tourniquet (in the direction of the arrows) to constrict the cord 3000 around the appendage. Suitably, the cord 3000 may be put in the anchor slot to maintain the tightness for an extended period of time.

Figure 14:
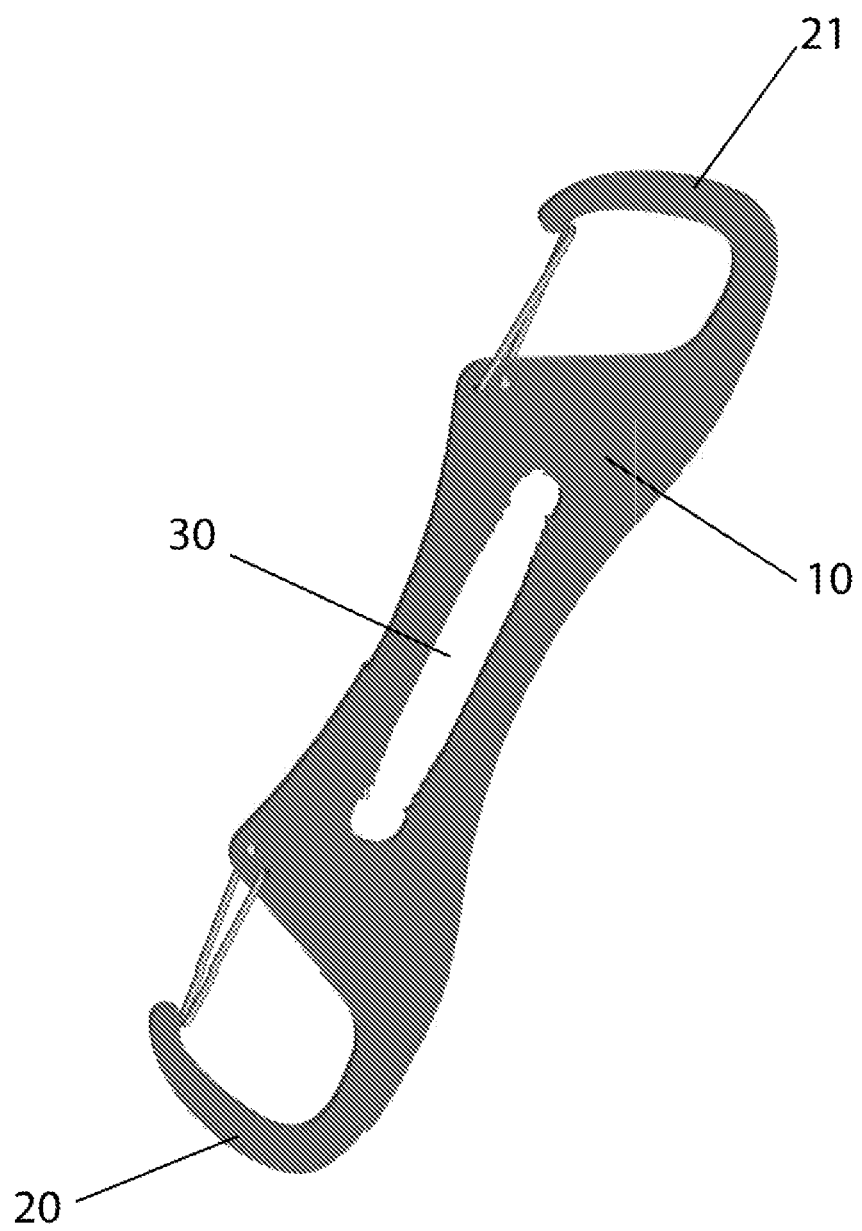
FIG. 14 is a perspective view of one embodiment of the tourniquet device.

FIG. 14 is a perspective view of one embodiment of a tourniquet device 10 for a surf leash. Components of the tourniquet device include a first receiver 20, a second receiver 21, and a fixed opening/slit 30, wherein the first and second receiver 20, 21 may be carabiner clips.

Figure 15:
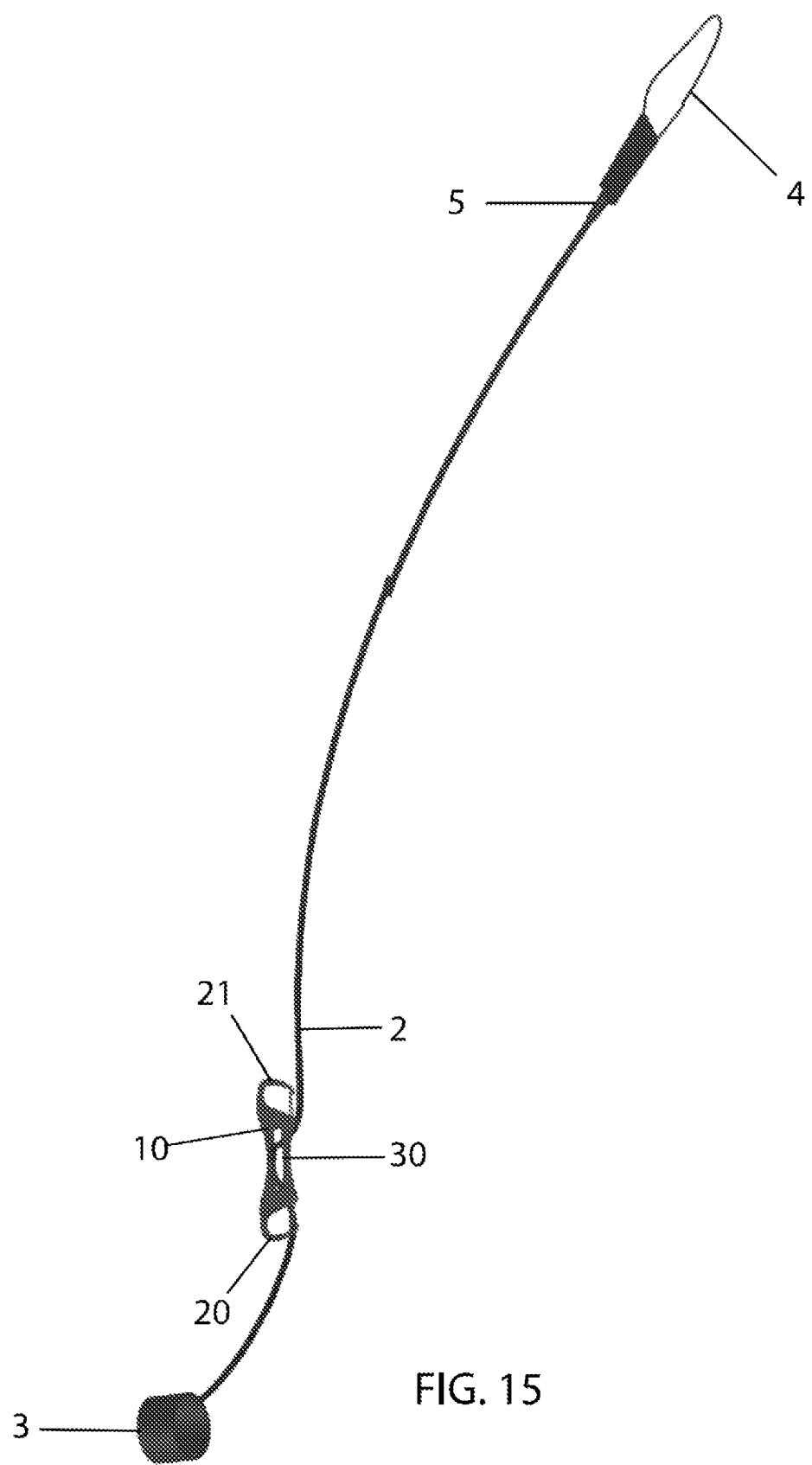
FIG. 15 is a perspective view of one embodiment of a surf leash tourniquet configured to function as a tourniquet.

FIG. 15 is a perspective view of one embodiment of a surf leash 1 with a tourniquet device 10. The surf leash 1 may be comprised of a cord 2, a cuff 3, a rail saver 4, and a swivel 5. Referring to FIG. 15, in one embodiment, the tourniquet device 10 may be suitably implemented along the length of the cord 2. The surf leash 1 may be used as a tourniquet to constrict or compress an extremity by threading a portion of the cord 2 through the slit 30, which allows the cord 2 to be pulled independently through the tourniquet device 10 and create a loop to surround an extremity, such as a severed leg or arm. Referring to FIG. 15, in use, the cord 2 is pulled through the slit 30, where the cord 2 creates a loop that extends from the slit 30 of the tourniquet device 10. Once there is enough slack in the loop to slide an extremity through, the cord 2 can be drawn back through the slit 30 on either side of the tourniquet device 10, or the tourniquet device 10 can slide along the cord 2 toward the extremity in the loop, to tighten the loop to the desired compression. The tourniquet device 10 can be rotated around the base of the loop to secure the cord 2 and loop in place. Once the desired amount of constriction is achieved, the user may wrap the excess cord 2 around the first and second receivers 20, 21 to maintain the tightness for a period of time.

Figure 16:
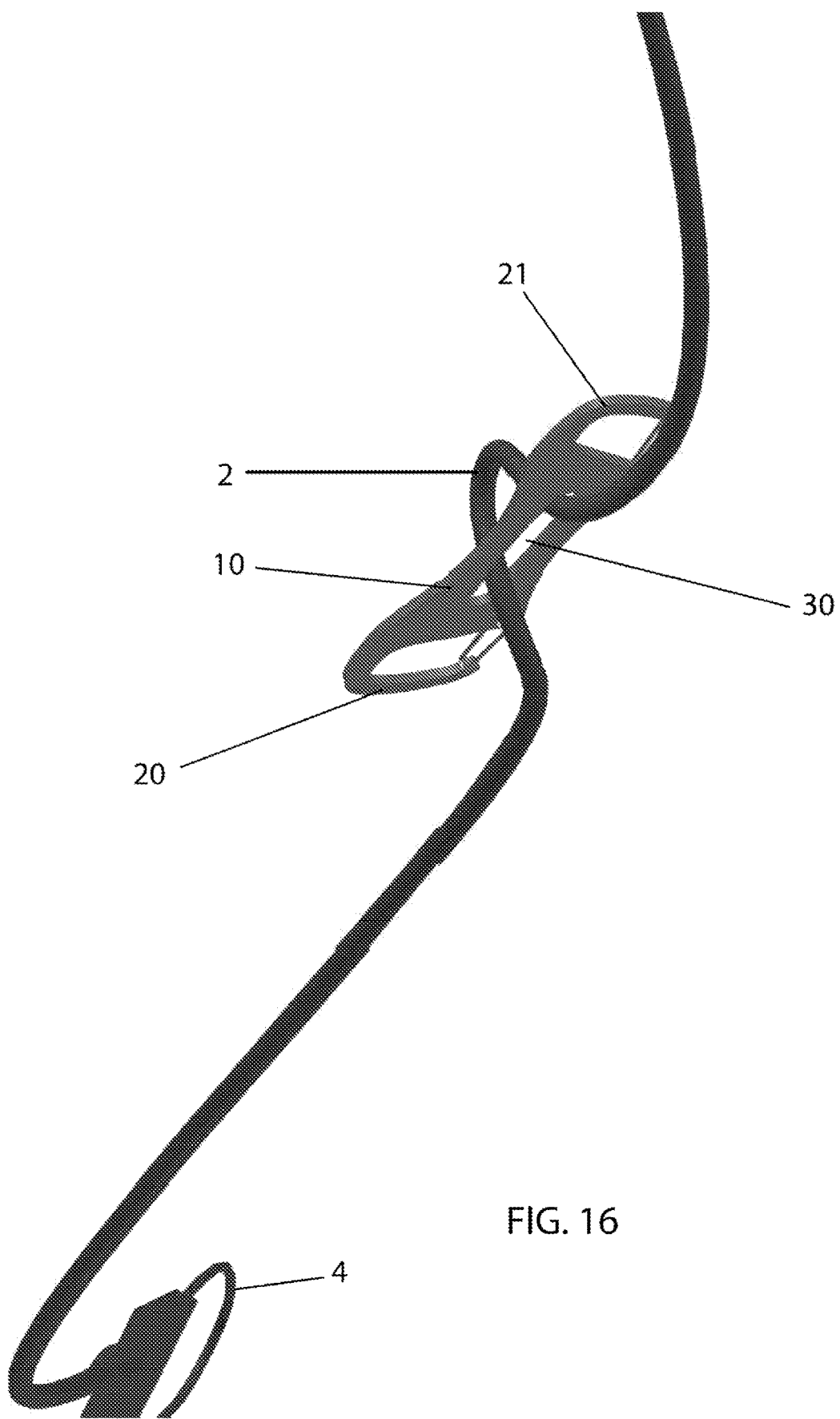
FIG. 16 is a perspective view of one embodiment of the surf leash tourniquet configured to function as a tourniquet.

FIG. 16 is a perspective view of one embodiment of the surf leash tourniquet, wherein, as explained above, a loop is created by threading a portion of the cord 2 through the slit 30 of the tourniquet device 10. The device 10 may be rotated to constrict the cord around an extremity.

Figure 17:
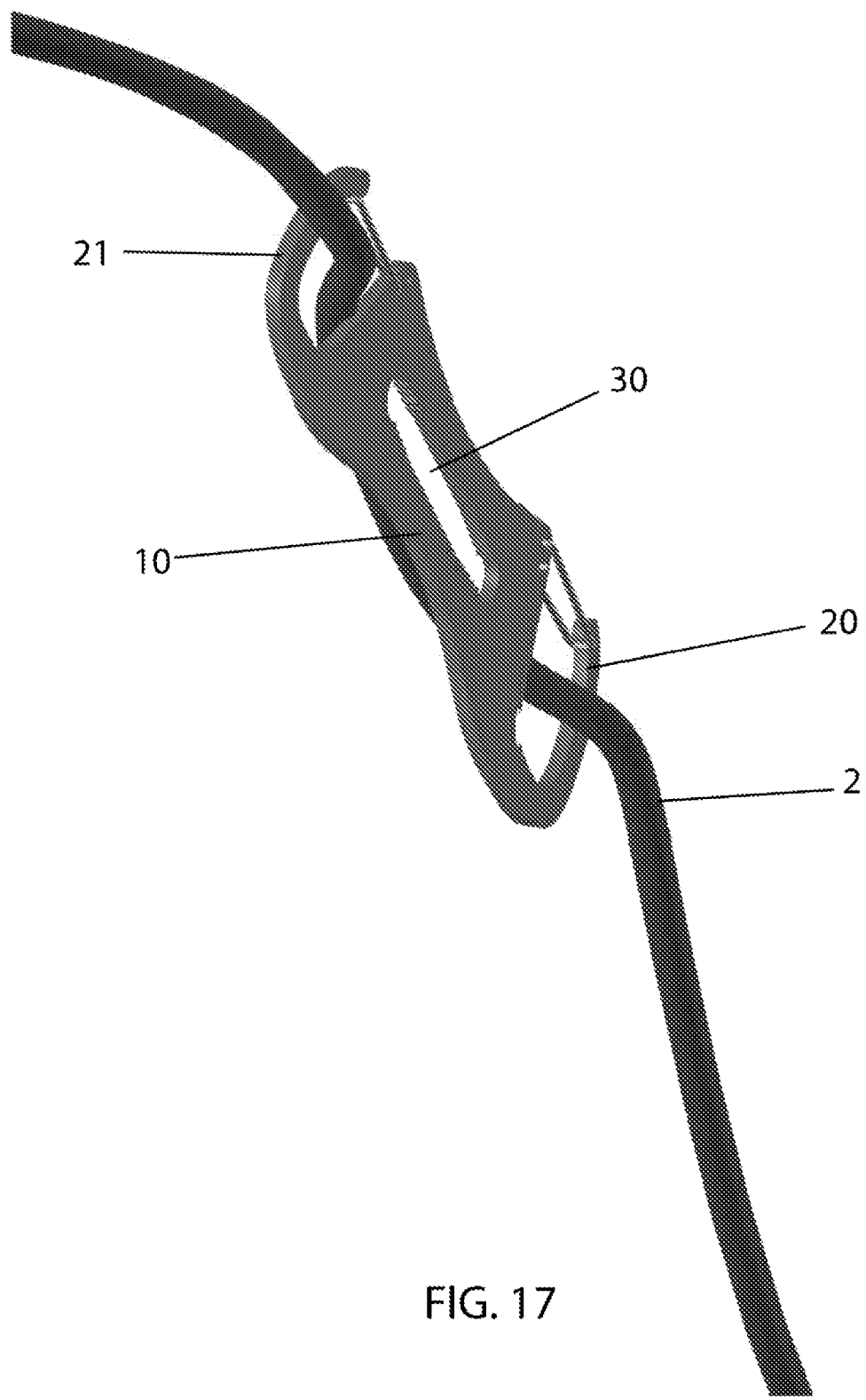
FIG. 17 is a perspective view of one embodiment of the surf leash tourniquet with a tourniquet device disposed along the surf leash.

FIG. 17 is a perspective view of one embodiment of the surf leash tourniquet. In this embodiment, the tourniquet device 10 may be implemented or disposed along the cord 2 of a surf leash 1 by inserting or clipping the cord 2 into a first receiver 20 and another portion of the cord 2 into the second receiver 21. Referring to FIG. 16, in one embodiment, once the cord 2 is inserted or clipped into the first receiver 20 and second receiver 21 respectively, a portion of the cord 2 that is between the first and second receiver 20, 21 is on the same side of the tourniquet device 10 and the cord 2 forms a loop with the tourniquet device 10.

Figure 18:
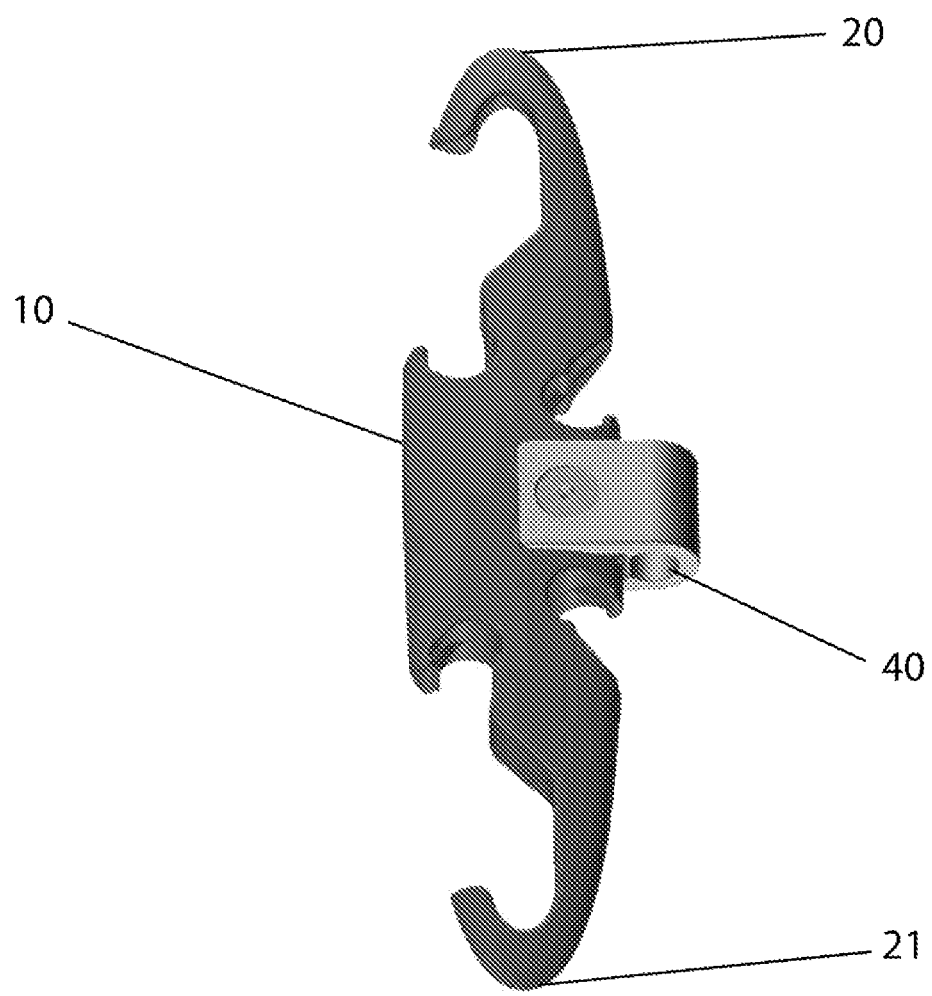
FIG. 18 is a perspective view of an alternative embodiment of the tourniquet device; and,
FIG. 19 is a perspective view of an alternative embodiment of the surf leash tourniquet.

FIG. 18 is a perspective view of another embodiment of the tourniquet device 10. In one embodiment the tourniquet device 10 may be composed of a first receiver 20, a second receiver 21, and a bore 40, wherein the first and second receiver 20, 21 may be hooks.

Figure 19:
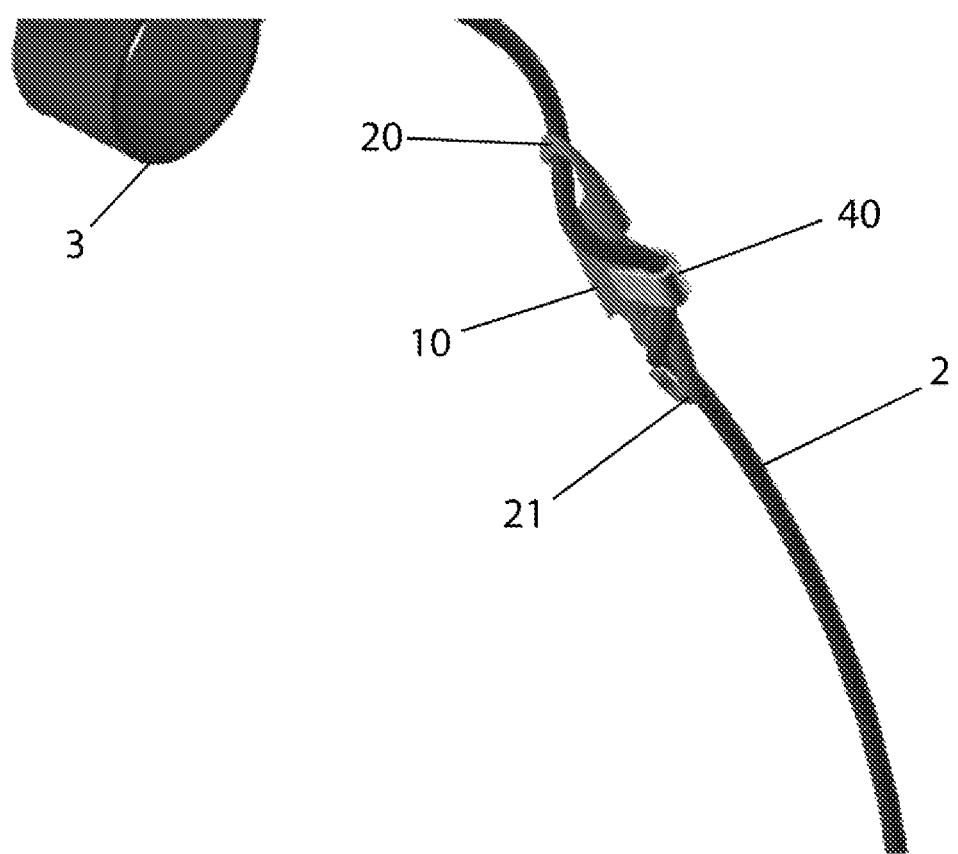

FIG. 19 is a perspective view of one embodiment of the surf leash tourniquet of FIG. 18. Referring to FIG. 19, a tourniquet device 10 may be disposed along a surf leash by threading the cord 2 through the bore 40 of a tourniquet device 10 and threading the cord 2 along the hooks of the first and second receiver 20, 21. A user may use the surf leash as a tourniquet by wrapping the cord 2 around the extremity to a desired tightness and then wrapping the excess cord 2 around the hooks of the first and second receiver 20, 21 to maintain the tightness for an extended period of time. In this embodiment, the device 10 would be appended to the leash cord 2, whereas other devices may be separate units operationally configured to work with existing surf leashes.

In one embodiment of the surf leash 1, the cord 2 may composed of a urethane material or any chemical construction that allows the cord 2 to be flexible and resilient. The tourniquet device 10 may be composed of any rigid plastic or metal material.

It should be noted that the above description and recited embodiments or examples are of illustrative importance only. In other words, the descriptions of the present disclosure should not be construed as limiting of the subject matter in this application. Additional modifications may become apparent to one skilled in the art after reading this disclosure. It should be further noted, that while the improvements are useful to surfers especially, the device and methods of using it to curb blood loss may admit to use by other persons who have access to cords or ropes, and who need a tool to make a quick tourniquet.

All original claims are hereby incorporated b reference.

We claim:

1. A method of using a tourniquet device (1000) comprising:
locating the tourniquet device (1000) that is defined by a concave elliptical disk with a first receiver (1020) and a second receiver (1021) defined along the semi-major axes of the elliptical disk, a bore (1040) centrally positioned on the elliptical disk, at least one anchor slot (1050) defined by an oblique cutout relative to the semi-minor and semi-major axes of the elliptical disk, a scraper (1060) defined by an edge of the disk, and a plurality of teeth (1070) defined along another edge of the disk;

attaching the tourniquet device (1000) to a surf leash cord (3000) by passing the cord through the bore (1040) of the tourniquet device (1000) so that the cord (3000) is threaded through both the bore (1040) and along the first and second receivers (1020,1021);

securing the cord (3000) to a surfboard (2000);

wrapping the cord (3000) around an extremity or appendage (4000);

securing the cord (3000) around the extremity or appendage (4000) by threading the cord (3000) in the first receiver and the at least one anchor slot (1050);

rotating the tourniquet device (1000) to constrict the cord (3000) around the extremity or appendage (4000); and anchoring the cord (3000) in the second receiver (1021).

2. The method of claim 1 wherein the tourniquet device (1000) features a body that is formed of the concave elliptical disk wherein the bore (1040) and the receivers (1020, 1021) are positioned in substantial alignment, whereby the cord (3000) can pass through either or both receivers (1020, 1021) and the bore (1040) in a substantially unobstructed manner.

\* \* \* \* \*